US010799429B2

(12) United States Patent
Claussen et al.

(10) Patent No.: US 10,799,429 B2
(45) Date of Patent: Oct. 13, 2020

(54) KIT OF PARTS FOR PRODUCING A PASTE TYPE GLASS IONOMER CEMENT, PROCESS OF PRODUCTION AND USE THEREOF

(71) Applicant: 3M INNOVATIVE PROPERTIES COMPANY, St. Paul, MN (US)

(72) Inventors: Kai U. Claussen, Munich (DE); Johannes M. Leykauff, Unterhausen (DE); Christine Lienau, Diessen (DE); Reinhold Hecht, Kaufering (DE); Peter Braun, Penzing (DE); Markus Mikulla, Andechs-Frieding (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 116 days.

(21) Appl. No.: 16/078,069

(22) PCT Filed: Feb. 16, 2017

(86) PCT No.: PCT/US2017/018028
§ 371 (c)(1),
(2) Date: Aug. 21, 2018

(87) PCT Pub. No.: WO2017/146968
PCT Pub. Date: Aug. 31, 2017

(65) Prior Publication Data
US 2019/0046419 A1 Feb. 14, 2019

(30) Foreign Application Priority Data
Feb. 25, 2016 (EP) .................................... 16157303

(51) Int. Cl.
| A61K 6/853 | (2020.01) |
| A61K 6/54 | (2020.01) |
| A61K 6/76 | (2020.01) |
| A61K 6/80 | (2020.01) |
| A61K 6/889 | (2020.01) |
| A61K 6/898 | (2020.01) |
| A61C 5/50 | (2017.01) |
| A61C 5/00 | (2017.01) |

(52) U.S. Cl.
CPC ................ *A61K 6/853* (2020.01); *A61C 5/00* (2013.01); *A61C 5/50* (2017.02); *A61K 6/54* (2020.01); *A61K 6/76* (2020.01); *A61K 6/80* (2020.01); *A61K 6/889* (2020.01); *A61K 6/898* (2020.01)

(58) Field of Classification Search
None
See application file for complete search history.

(56) References Cited

U.S. PATENT DOCUMENTS

| 4,209,434 A * | 6/1980 | Wilson | C08K 3/40 524/443 |
| 4,337,186 A * | 6/1982 | Crisp | A61K 6/889 525/362 |
| 4,360,605 A * | 11/1982 | Schmitt | A61K 6/889 523/116 |
| 4,569,954 A * | 2/1986 | Wilson | A61K 6/20 523/116 |
| 5,151,453 A * | 9/1992 | Ibsen | A61K 6/887 522/14 |
| 5,520,922 A * | 5/1996 | Gasser | C08K 3/16 424/422 |
| 5,814,682 A * | 9/1998 | Rusin | A61K 6/30 523/116 |
| 5,918,772 A * | 7/1999 | Keller | B05C 17/00506 222/145.5 |
| 5,944,419 A * | 8/1999 | Streiff | B01F 5/0641 366/337 |
| 5,965,632 A * | 10/1999 | Orlowski | A61K 6/889 523/116 |
| 6,479,038 B1 * | 11/2002 | Day | A61K 8/042 424/49 |
| 6,719,834 B1 * | 4/2004 | Braun | A61K 6/889 106/35 |
| 6,765,038 B2 * | 7/2004 | Mitra | A61K 6/889 523/115 |
| 6,872,244 B2 * | 3/2005 | Kobayashi | C04B 28/28 106/35 |
| 7,329,702 B2 * | 2/2008 | Nelson | C01B 33/44 501/145 |
| 8,362,134 B2 * | 1/2013 | Grah | C01B 33/44 206/524.2 |
| 2004/0067359 A1 * | 4/2004 | Hirasawa | C03C 17/30 428/391 |
| 2006/0187752 A1 * | 8/2006 | Keller | B01F 5/0617 366/337 |

(Continued)

FOREIGN PATENT DOCUMENTS

| DE | 4433811 | 3/1996 |
| EP | 0510211 | 10/1992 |

(Continued)

OTHER PUBLICATIONS

Database Registry, Chemical Abstracts Service, 1984, 2pages.

(Continued)

*Primary Examiner* — Peter A Salamon
(74) *Attorney, Agent, or Firm* — 3M IPC

(57) ABSTRACT

The invention relates to a kit of parts for preparing a glass ionomer composition for dental use, the kit comprising a Paste A and a Paste B, Paste A comprising water, acid-reactive inorganic filler A, phyllo silicate(s), Paste B comprising water, poly-acid, non acid-reactive filler B, optionally chelating agent. The invention also relates to a hardenable composition obtainable by combining the pastes of the kit or parts and to the use of such a composition as or for preparing a dental cement, dental filling material, dental core build up material or dental root channel filling material.

15 Claims, No Drawings

(56) References Cited

U.S. PATENT DOCUMENTS

| | | | | |
|---|---|---|---|---|
| 2007/0072957 | A1* | 3/2007 | Noguchi | A61K 6/889 523/116 |
| 2007/0090079 | A1* | 4/2007 | Kelller | B65D 39/16 215/211 |
| 2007/0254998 | A1* | 11/2007 | Orlowski | A61K 6/30 524/425 |
| 2009/0297675 | A1* | 12/2009 | Grah | C01B 33/44 426/125 |
| 2012/0295214 | A1* | 11/2012 | Wang | A61C 5/62 433/24 |
| 2019/0046419 | A1* | 2/2019 | Claussen | A61C 5/00 |

FOREIGN PATENT DOCUMENTS

| | | |
|---|---|---|
| EP | 0967956 | 1/2000 |
| EP | 2163233 | 3/2010 |
| GB | 2021123 | 11/1979 |
| JP | 4132809 | 7/2003 |
| RU | 2308259 | 10/2007 |
| WO | 2005-016783 | 2/2005 |
| WO | 2007-104037 | 9/2007 |
| WO | 2008-096011 | 8/2008 |
| WO | 2009-061884 | 5/2009 |
| WO | 2010-123800 | 10/2010 |
| WO | 2015-005880 | 1/2015 |

OTHER PUBLICATIONS

Ullmann's Encyclopedia of Industrial Chemistry, Silicates. Table 4, Wiley-VCH, 2005, vol. 32, pp. 370.
International Search report for PCT International Application No. PCT/US2017/018028 dated Apr. 10, 2017, 5 pages.

* cited by examiner

KIT OF PARTS FOR PRODUCING A PASTE TYPE GLASS IONOMER CEMENT, PROCESS OF PRODUCTION AND USE THEREOF

FIELD OF THE INVENTION

The invention relates to a kit of parts for producing a glass ionomer cement (GIC), wherein the cement is obtainable by mixing two pastes.

BACKGROUND ART

Glass ionomer cements have been used for more than 30 years for dental restorative treatments.
Typically, glass ionomer cements are provided as powder/liquid system.
In general, the powder part comprises an alkaline, reactive glass powder and the liquid part comprises a polyacid dissolved in water.
After mixing, the polyacid acid is neutralized by the alkaline glass powder. In the process of neutralization, ions such as $Ca^{2+}$, $Sr^{2+}$ or $Al^{3+}$ are leached out of the alkaline glass powder. These ions subsequently crosslink the deprotonated polyacid, leading to hardening of the mixture which ultimately results in a cured material.
If no mixing device is available, hand mixing of the powder and the liquid is often challenging for the practitioner due to an exhausting protocol which needs to be followed to obtain a homogeneous mixture that is free of powder agglomerates and/or air inclusions.
As a consequence, the practitioner often does not use the powder and liquid part in the recommended ratio, but intentionally decreases the viscosity of the mixture by using an excess of the liquid part to make hand mixing more convenient.
However, this alteration often results in lower mechanical properties which, in return, may negatively affect long-term performance and furthermore may increase the number of product complaints.
Therefore, a paste/paste system with its inherent easy mixing capability would be beneficial and is thus highly desired.
One way to transform a traditional powder/liquid into a paste/paste system is by adding (a) water to the powder part and (b) non-reactive filler to the liquid part.
Unfortunately, the simple addition of water to glass powder often results in a rheopectic paste which is unfavorable for mixing purposes.
Moreover, the addition of non-reactive filler to the liquid part is not trivial, either, because some fillers, even if classified as inert, slowly react with polyacids. This may result in an insufficient shelf-life due to an increase of the viscosity of the respective paste over time.
In the patent literature different approaches are described trying to address these issues.
U.S. Pat. No. 6,719,834 (Braun et al.) relates to a polyelectrolyte cement containing at least two reaction partners: a) at least one metal-cation-releasing compound and b) one or more polyelectrolyte capable of being converted into a solid state, wherein at least one of the polyelectrolytes is at least partially water soluble and wherein at least a part of the reaction partners (a) and/or (b) is coated with an organic surface-coating agent. The polyelectrolyte cement is stable in storage and can be easily mixed.
US 2007/0072957 A1 (Noguchi et al.) describes a dental paste glass ionomer cement composition comprising a first paste and a second paste, the first paste comprising i.a. 20 to 60 wt. % of an unsaturated carboxylic acid polymer, 10 to 60 w.-% filler that is not reacted with the unsaturated carboxylic acid polymer and is not in a monodisperse state in water, 0.1 to 10 wt. % colloidal silica, 20 to 60 wt. % water, the second paste comprising 50 to 85 wt. % fluoroalumino silicate glass powder, 0.01 to 10 wt. % thickening agent and 20 to 45 wt. % water.
US 2007/0254998 A1 (Orlowski et al.) relates to a two-part glass ionomer composition comprising (1) an aqueous paste or viscous liquid made from acrylic acid monomers with an inorganic filler (up to 30 wt. %) comprising quartz, glass, aluminum oxide, silica or any combination and (2) a paste comprising basic glass, water-soluble/miscible monomers or prepolymers having at least one hydroxyl group.
U.S. Pat. No. 6,872,244 B2 (Kobayashi et al.) describes a two paste cement composition. The first paste contains a polyacrylic polymer and water and (2) the second paste contains a fluoroaluminosilicate glass, a water-soluble thickening agent and water.
U.S. Pat. No. 5,965,632 (Orlowski et al.) relates to a two paste glass ionomer dental cement system with both pastes being preferably of similar consistency. The first paste contains an inert inorganic filler selected from quartz, glass, aluminum oxide, silica or any combination or an inorganic filler selected from quartz, glass, $SiO_2$, aluminum oxide, zirconium oxide and any combination, an aqueous solution of polyacrylic acid or its copolymers and various additives and a second paste containing an alkaline, fluoride-containing glass suspended in an aqueous solution of a hydrophilic acrylic monomer or polymer and up to 10 wt. % of an inert inorganic filler selected from quartz, glass, aluminum oxide or any combination. Organic or inorganic thickening agents such as hydroxyalkyl cellulose, hydrophilic silica, polyacrylic acid or polyvinyl pyrollidone can be added to both pastes to achieve a desirable consistency.
U.S. Pat. No. 5,814,682 (Rusin et al.) describes a method of luting a provisional prosthetic device to tooth structure with a glass ionomer cement system with up to three pastes A, B and C. After mixing of paste A with either paste B or paste C, a dental cement is obtained with different mechanical properties. The first paste contains a water-miscible acidic polymer, the second paste contains an acid-reactive filler to obtain low shear adhesion in the resulting cement and the third paste comprises an acid-reactive filler to obtain high shear adhesion in the resulting cement.
US 2012/0295214 A1 (Wang et al.) describes a method of dispensing a hardenable dental composition comprising a first paste with acid-reactive glass, a liquid such as water and a monomer and any combination thereof and a second paste with a water-miscible polyacid, a liquid such as water and a monomer and any combination thereof.
EP 2 163 233 B1 (Kato et al.) relates to a paste-type dental cement comprising (1) a first paste with fluoroaluminosilicate (FAS) glass powder, a liquid component no reacting with the FAS glass, the liquid being one member selected from the group consisting of polyhydric alcohol, alcohol, acetone, or dioxane, a water, and a fluorescent agent and (2) a second paste comprising phosphoric acid and/or a carboxylic polyacid, water, and a powder not reacting with acid.
EP 0 510 211 A1 (Masuhara et al.) describes a glass ionomer cement system comprising (1) a paste with 55-90 wt. % glass powder, 0.1-2.0 wt. % water-soluble polymer and 9.9-44.9 wt. % water and (2) a liquid with 40-75 wt. % polycarboxylic acid or a copolymer.
GB 2 021 123 A (Harvey et al.) relates to a surgical cement useful in dentistry which is formed by mixing (a) a concentrated non-gelling aqueous solution of polycarboxylic acid and (b) an aqueous suspension of metal oxide or polyvalent-cation-containing glass powder. Preferably both (a) and (b) are provided as pastes. As possible thickener colloidal bentonite or water soluble resins and gums like methyl cellulose are mentioned.

U.S. Pat. No. 4,337,186 (Crisp et al.) relates to powder/liquid compositions which are hardenable in the presence of water to form a poly(carboxylate) cement containing a metal salt which accelerates the setting of the composition.

However, none of the proposed solutions is completely satisfying.

DESCRIPTION OF THE INVENTION

Thus, it is an objective of the invention to provide a glass ionomer cement, which can easily be mixed even at high shear rates and shows adequate physical properties after hardening (like flexural and/or compressive strength).

Ideally, the glass ionomer cement can be provided as a shelf-life stable product.

Sometimes it is also desirable, if the components of a glass ionomer cement can easily be deployed from a packaging device.

This object can be achieved by the kit of parts and the glass ionomer cement composition obtained or obtainable when mixing the pastes of the kit of parts as described in the claims and the present text.

According to one embodiment, the kit of parts for preparing a glass ionomer composition for dental use comprises a Paste A and a Paste B, Paste A comprising
water,
acid-reactive inorganic filler A,
phyllo silicate(s), in particular phyllo silicate selected from 2:1 layer silicates and
comprising calcium ions and sodium ions,
Paste B comprising
water,
polyacid,
chelating or complexing agent,
non acid-reactive filler B.

The invention is also directed to a device for storing the kit of parts described in the present text, the device comprising two compartments, Compartment A and Compartment B, Compartment A containing Paste A and Compartment B containing Paste B, Paste A and Paste B being as described in the present text, Compartment A and Compartment B both comprising a nozzle or an interface for receiving an entrance orifice of a static mixing tip.

Moreover, the invention features a method of using the kit of parts and the cement composition obtainable or being obtained by mixing the respective pastes as described in the present text for dental purposes, in particular as dental cement, dental filling material, dental core build up material or dental root channel filling material.

According to a further embodiment the invention is directed to the use of phyllo silicates as described in the present text for producing paste type glass ionomer cement compositions, in particular for producing storage stable glass ionomer cement compositions.

According to a further embodiment the invention is directed to the use of phyllo silicates as described in the present text a paste former for paste type glass ionomer cements in particular those described in the present text.

Definitions

Unless defined differently, for this description the following terms shall have the given meaning:

A "dental composition" or a "composition for dental use" or a "composition to be used in the dental field" is any composition which can be used in the dental field. In this respect the composition should be not detrimental to the patients' health and thus free of hazardous and toxic components being able to migrate out of the composition. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

A "polymerizable component" is any component which can be cured or solidified e.g. by heating to cause polymerization or chemical crosslinking, or e.g. by radiation-induced polymerization or crosslinking, or e.g. using a redox initiator. A polymerizable component may contain only one, two, three or more polymerizable groups. Typical examples of polymerizable groups include unsaturated carbon groups, such as a vinyl group being present e.g. in a (methyl)acrylate group.

The cement composition described in the present text does not contain polymerizable components in an amount above about 0.5 or 1 wt. % with respect to the whole composition. The cement composition described in the present text is essentially free of polymerizable components bearing (meth)acrylate groups.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth)acryloxy" group is a shorthand term referring to either an acryloxy group (i.e., $CH_2$=CH—C(O)—O—) and/or a methacryloxy group (i.e., $CH_2$=C($CH_3$)—C(O)—O—).

An "initiator" is a substance being able to start or initiate the curing process of polymerizable components or monomers, e.g. redox/auto-cure chemical reaction or by a radiation induced reaction or by a heat induced reaction.

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term "d50/µm" with regard to particle size measurement means that 50% of the particles in the analyzed volume, the particles have a size below x μm. E.g., a particle size value of below 100 μm (d50) means that within the analyzed volume, 50% of the particles have a size below 100 μm.

"Paste" shall mean a soft, viscous mass of solids dispersed in a liquid. "Viscous" means a viscosity above about 50 Pa*s (at 23° C.).

A "liquid" means any solvent or liquid which is able to at least partially disperse or dissolve a component at ambient conditions (e.g. 23° C.). A liquid typically has a viscosity below about 10 or below about 8 or below about 6 Pa*s.

"Glass ionomer cement" or "GIC" shall mean a cement curing or hardening by the reaction between an acid-reactive glass and a polyacid in the presence of water.

"Resin modified glass ionomer cement" or "RM-GIC" shall mean a GIC containing in addition polymerizable component(s), an initiator system and typically 2-hydroxyl-ethyl-methacrylate (HEMA).

"Acid-reactive filler" shall mean a filler that chemically reacts in the presence of a (poly)acid leading to a hardening reaction.

"Non acid-reactive filler": shall mean a filler, which does not show a chemical hardening reaction within 30 min, if mixed with a (poly)acid at ambient conditions (e.g. 23° C.).

To distinguish an acid-reactive filler from a non acid-reactive filler the following test can or is to be conducted: A composition is prepared by mixing Part A with Part B in a mass ratio of 3 to 1, wherein: Part A contains: filler to be analyzed: 100 wt. %; Part B contains: poly (acrylic acid co maleic acid) (Mw: about 20,000+/−3,000): 43.6 wt. %, water: 47.2 wt. %, tartaric acid: 9.1 wt. %, benzoic acid: 0.1 wt. %.

Examples of non acid-reactive fillers include quartz glass or strontium oxide based glasses. Further examples are given in the text below.

"Cation reduced aluminosilicate glasses" shall mean a glass having a lower content of cations in the surface region of the glass particle compared with the inner region of the glass particle. These glasses react much slower upon contact with a solution of polyacrylic acid in water as compared to typical acid-reactive fillers. Cation reduction can be achieved by a surface treatment of the glass particles. Suitable surface treatments include, but are not limited to, acid washing (e.g., treatment with a phosphoric acid), treatment with a phosphate, treatment with a chelating agent such as tartaric acid, and treatment with a silane or an acidic or basic silanol solution.

"Polyacid" or "polyalkenoic acid" shall mean a polymer having a plurality of acidic repeating units (e.g. more than 10 or more than 20 or more than 50). That is, the acidic repeating units are attached to or pending from the backbone of the polymer.

"Complexing or chelating agent" shall mean a low molecular agent comprising moieties and being able to form a complex with metal ions like calcium or magnesium; e.g. tartaric acid.

"Phyllo silicates" are silicates forming sheets of silicate tetrahedra with $Si_2O_5$. Phyllo silicates can be further divided in sub-groups, e.g. according to the number of sheets or layers arranged with each other.

Phyllo silicates can be divided by the number of silicate layers. With respect to this classification a more detailed description can be found in Ullmanns Encyclopedia of Industrial Chemistry (Wiley-VCH), 2005, Silicates; especially table 4.

A "storage stable composition" is a composition which can be stored for an adequate period of time (e.g. at least about 12 months under ambient conditions) without showing significant performance issues (e.g. reduced flexural or compressive strength), and/or which does not harden over time and/or which does not separate over time. A suitable test for determining the storage stability is given in the Example section below.

By "hardenable" or "curable" is meant that the composition can be cured or solidified, e.g. by conducting a glass ionomer cement reaction without the need for an additional curing system like chemical cross-linking, radiation-induced polymerization or crosslinking.

A composition is "essentially or substantially free of" a certain component, if the composition does not contain said component as an essential feature. Thus, said component is not wilfully added to the composition either as such or in combination with other components or ingredient of other components.

A composition being essentially free of a certain component usually contains the component in an amount of less than about 1 wt. % or less than about 0.5 wt. % or less than about 0.1 wt. % or less than about 0.01 wt. % with respect to the whole composition or material. The composition may not contain the said component at all. However, sometimes the presence of a small amount of the said component is not avoidable e.g. due to impurities contained in the raw materials used.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably.

The terms "comprises" or "contains" and variations thereof do not have a limiting meaning where these terms appear in the description and claims. The term "comprising" also includes the more limited expressions "consisting essentially of" and "consisting of".

Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about."

DETAILED DESCRIPTION

The kit of parts for producing a paste type glass ionomer cement composition described in the present text has a couple of advantageous properties.

While conventional glass ionomer materials are usually offered as a powder/liquid system, a paste/paste system not only simplifies the hand-mixing procedure of the two components, it also enables the application of so-called automix systems, where the two components are mixed e.g. by using a static mixing device.

In order to be adequately mixed in an automix system, the respective pastes need to have an adequate viscosity. If the viscosity is too high, it may become difficult to press the pastes through a static mixing cannula.

For adjusting the viscosity, typically a solvent like water and a thickening or paste forming agent are added to the composition.

A lot of thickening agents suggested in the prior art are water-soluble and consequently require a sufficient amount of water to form gel-like structures in which the glass powder can be homogenously distributed.

If, however, the water content becomes too high, a decrease of mechanical properties of the hardened composition may result.

It was found that by diligently selecting a specific class of thickening or paste forming agents, it is possible to transform a conventional powder/liquid system used for producing glass ionomer cements into a paste/paste system.

The phyllo silicates used for formulating the kit of parts or glass ionomer cement described in the present text are not water soluble and were found to be particularly useful for solving one or more of the above objects. Mixing the respective pastes even at high shear rates is now possible.

The respective pastes of the kit of parts can also be deployed easily from packaging devices.

However, despite the fact that a further component is added, the obtained glass ionomer cement composition described in the present text shows adequate mechanical properties after hardening.

The mechanical properties are sometimes even superior over the mechanical properties reported in the prior art for other glass ionomer cement obtained from a paste/paste system.

This is surprising as due to the additional liquid component which is needed for transferring a powder to a paste, the mechanical properties of the resulting cement obtained from a paste/paste system are expected to be lower compared to the mechanical properties of a cement obtained from a powder/liquid system.

If desired, the glass ionomer cement described in the present text can also be provided in a so-called automix system and can be delivered from such a system at low extrusion forces.

Furthermore, it was found that the respective pastes are storage stable, i.e. they do not show phase separation during storage, even if the pastes have a considerable low viscosity.

If the phyllo silicates of the present invention were used, the respective pastes showed less segregation of its components during storage, in particular as regards the amount of water.

The kit of parts described in the present text comprises two pastes. Upon mixing those two pastes, a composition in the form of a further paste is obtained. That composition hardens by a so-called glass ionomer cement reaction.

The kit of parts described in the present text comprises a Paste A.

Paste A contains water.

The water can be distilled, de-ionized, or plain tap water. Typically, de-ionized water is used.

The amount of water should be sufficient to provide adequate handling and mixing properties and to permit the transport of ions, particularly in the cement reaction.

Water is typically present in the following amount:
Lower limit: at least 5 or at least 7 or at least 10 wt. %;
Upper limit: utmost 45 or utmost 40 or utmost 35 wt. %;
Range: from 5 to 45 or from 7 to 40 or from 10 to 35 wt. %;
wt. % with respect to the weight of Paste A.

If the amount of the water is too low, obtaining a workable consistency of the obtained paste might become difficult.

If the amount of water is too high, obtaining a workable consistency of the obtained paste might become difficult, too. Furthermore, it will become difficult to achieve the desired mechanical properties and the paste might separate during storage.

Paste A contains an acid-reactive inorganic filler A.

The nature and structure of the acid-reactive filler A is not particularly limited unless the desired result cannot be achieved. The acid-reactive filler A has to be able to undergo a glass-ionomer cement reaction.

According to one embodiment, the acid-reactive filler A can be characterized by at least one or more or all of the following parameters:
Mean particle size: 1 to 25 μm;
(d10/μm): from 0.5 μm to 3 μm; (d50/μm): from 2 μm to 7 μm; (d90/μm): from 6 μm to 15 μm;
pH value of a dispersion of 1 g filler stirred in 10 ml de-ionized water (having a pH of about 5) for 5 minutes: between 5 and 8 or between 5 and 7.

If the mean particle size of the acid-reactive filler A is above the range outlined above, the consistency of the composition obtained when mixing the compositions contained in the parts of the kit of parts described in the present text will not be adequate and the desired mechanical properties might be negatively affected.

If the mean particle size of the acid-reactive filler A is below the range outlined above, the setting time will be too fast.

Suitable acid-reactive fillers A include metal oxides, metal hydroxides, hydroxyapatite, acid-reactive glasses including aluminosilicate glasses and fluoroaluminosilicate glasses.

Typical metal oxides include barium oxide, strontium oxide, calcium oxide, magnesium oxide, zinc oxide.

Typical metal hydroxides include calcium hydroxide, magnesium hydroxide, strontium hydroxide and mixtures thereof.

Typical acid-reactive glasses include aluminosilicate glasses and in particular fluoro-aluminasilicate ("FAS") glasses.

FAS glasses are particularly preferred. The FAS glass typically contains a sufficient amount of elutable cations so that a hardened dental composition can be obtained when the glass is mixed with the other components of the hardenable composition.

The FAS glass also typically contains a sufficient amount of elutable fluoride ions so that the hardened composition will have anticariogenic properties.

The glass can be made from a melt containing fluoride, silica, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Suitable FAS glasses will be familiar to those skilled in the art, and are available from a wide variety of commercial sources, and many are found in currently available glass ionomer cements such as those commercially available under the trade designations Ketac™-Molar or Ketac™-Fil Plus (3M Oral Care, Seefeld, Germany), and FUJI™ IX (GC, Tokyo, Japan).

Fluoroaluminosilicate glasses can be prepared by fusing mixtures of silica, alumina, cryolite and fluorite.

Useful acid-reactive glasses can also be characterized by the Si/Al ratio. Fillers having a Si/Al ratio (by wt. %) of below 1.5 or 1.4 or 1.3 were found to be useful.

Suitable acid-reactive fillers are also commercially available from e.g. Schott AG (Germany) or Speciality Glass (US).

Mixtures of acid-reactive fillers A can be used, if desired.

The acid-reactive filler A is typically present in the following amount:

Lower limit: at least 45 or at least 50 or at least 55 wt. %;
Upper limit: utmost 95 or utmost 90 or utmost 85 wt. %;
Range: from 45 to 95 or from 50 to 90 or from 55 to 85 wt. %, wt. % with respect to the weight of Paste A.

If the amount of the acid-reactive filler is too high, mixing of the pastes of the kit of parts described in the present text may become more difficult. Furthermore, obtaining an adequate consistency and acceptable mechanical properties of the resulting composition might become difficult, as well. If the amount of the acid-reactive filler is too low, formulating a suitable paste might become more difficult. Furthermore, the mechanical properties might become inferior.

Paste A also comprises a phyllo silicate.

The phyllo silicate functions as rheological additive, in particular as an additive suitable for forming a paste.

According to one embodiment the phyllo silicates are selected from 2:1 layer silicates.

2:1 layer silicates include talc-pyrophyllite type minerals, smectite type minerals, vermiculite type minerals, illites type minerals, glimmer type minerals, mica type minerals and mixtures thereof.

2:1 layer silicates also include montmorillonite, bentonite, hectorite, talc, willemseite, pyrophyllite, stevensite, saponite, sauconite, beidellite, nontronite, volkonskite, phlogopite, biotite, lepidolite, muscovite, illite, glauconite, celadonite, and mixtures thereof.

Phyllo silicates typically contain ions located between the individual layers.

According to one embodiment the phyllo silicate is a 2:1 layer silicate containing calcium and/or sodium ions.

Without wishing to be bound to a particular theory, it is believed that in particular the phyllo silicates described above are able to absorb water in an amount sufficient to produce a storage stable paste and are thus sometimes preferred.

The use of 2:1 layer silicates containing calcium and sodium ions facilitates the production of storage stable paste/paste compositions with good mechanical properties, even if only a small amount of layer silicate was used.

The particle size of the phyllo silicate is not particularly limited.

The mean particle size is typically below about 100 μm, or below about 80 μm or below about 70 μm.

A 2 wt. % aqueous dispersion (de-ionized water having a pH of about 5) of the phyllo silicate typically has a pH value in the range of 5 to 11.

In particular phyllo silicates were found to be useful which are able to swell in water. If desired, the swelling properties can also be examined by x-ray diffraction analysis (XRD).

The phyllo silicate is typically present in the following amount:

Lower limit: at least 0.1 or at least 0.2 or at least 0.5 wt. %;
Upper limit: utmost 30 or utmost 25 or utmost 20 wt. %;
Range: from 0.1 to 30 or from 0.2 to 25 or from 0.5 to 20 wt. %, wt. % with respect to the weight of Paste A.

According to one embodiment, Paste A of the kit of parts described in the present text contains a 2:1 layer silicate in an amount from 0.1 to 15 wt. % or from 0.2 to 12 wt. % or from 0.2 to 10 wt. %, with respect to the weight of Paste A.

According to another embodiment, Paste A of the kit of parts described in the present text contains a 2:1 layer silicate in an amount from 0.1 to 2 wt. % or from 0.2 to 1.5 wt. % or from 0.2 to 1.2 wt. %, with respect to the weight of Paste A.

The ratio of acid-reactive inorganic filler to phyllo silicate is typically in a range from 10:1 to 1,000:1 or from 10:1 to 100:1 with respect to weight.

Paste A can typically be characterized by either, more or all of the following features:

Density: from 1.5 to 3.0 g/cm$^3$;
pH value: from 5 to 10 or 5 to 8 (determined with a pH indicator for 1 g Paste A being dispersed in 10 ml de-ionized water and stirred for 5 minutes),
being storage stable.

If desired, the storage stability can be determined as described in the example section.

Paste B contains water, too. The water contained in Paste B is as described for Paste A.

Water is typically present in the following amount:

Lower limit: at least 5 or at least 7 or at least 9 wt. %;
Upper limit: utmost 60 or utmost 55 or utmost 50 wt. %;
Range: from 5 to 60 or from 7 to 55 or from 9 to 50 wt. %;

wt. % with respect to the weight of Paste B.

Paste B contains a polyacid.

The nature and structure of the polyacid is not particularly limited, either, unless the desired result cannot be achieved. However, the polyacid should have a molecular weight sufficient to provide good storage, handling, and mixing properties, as well as to yield good material properties in the glass ionomer material.

According to one embodiment, the polyacid can be characterized by at least one or more or all of the following parameters:

Being a solid (at 23° C.);
Molecular weight (Mw): from about 2,000 to about 250,000 or from about 4,000 to about 100,000 (evaluated against a polyacrylic acid sodium salt standard using gel permeation chromatography).

If the molecular weight of the polyacid is too high, obtaining a workable consistency of the obtained paste when mixing the compositions contained in the kit of parts described in the present text might become difficult. Furthermore, preparation of the compositions might become difficult, too. In addition, the obtained mixture or composition might become too sticky (i.e. adheres to the dental instrument used for application).

If the molecular weight of the polyacid is too low, the viscosity of the obtained paste might become too low and the mechanical properties inferior.

Typically, the polyacid is a polymer having a plurality of acidic repeating units.

The polyacid to be used for the cement composition described in the present text is substantially free of polymerizable groups.

The polyacid need not be entirely water soluble, but typically it is at least sufficiently water-miscible so that it does not undergo substantial sedimentation when combined with other aqueous components.

The polyacid is hardenable in the presence of, for example, an acid-reactive filler and water, but does not contain ethylenically unsaturated groups.

That is, the polyacid is a polymer obtained by polymerising an unsaturated acid. However, due to the production process, a polyacid might still contain unavoidable traces of free monomers (e.g. up to 1 or 0.5 or 0.3 wt. % with respect to the amount of monomers used).

Typically, the unsaturated acid is an oxyacid (i.e., an oxygen containing acid) of carbon, sulfur, phosphorous, or boron. More typically, it is an oxyacid of carbon.

Suitable polyacids include, for example, polyalkenoic acids such as homopolymers and copolymers of unsaturated mono-, di-, or tricarboxylic acids.

Polyalkenoic acids can be prepared by the homopolymerization and copolymerization of unsaturated aliphatic carboxylic acids, e.g., acrylic acid, methacrylic acid, itaconic acid, maleic acid, glutaconic acid, aconitic acid, citraconic acid, mesaconic acid, fumaric acid, and tiglic acid.

Suitable polyacids also include alternating copolymers of maleic acid and ethylene (e.g. in a molar one to one ratio).

Suitable polyacids are also described in the following documents: U.S. Pat. No. 4,209,434 (Wilson et al.), U.S. Pat. No. 4,360,605 (Schmitt et al.). The content of these documents with respect to the description of the polyacid is herewith incorporated by reference.

Suitable polyacids are also included as aqueous solutions in the liquid component of commercially available products from e.g. 3M ESPE (e.g. Ketac™ Fil Plus Handmix) or GC (e.g. Fuji™ IX GP Handmix).

The amount of polyacid should be sufficient to react with the acid-reactive filler and to provide an ionomer composition with desirable hardening properties.

The polyacid is typically present in the following amount:
 Lower limit: at least 3 or at least 5 or at least 10 wt. %;
 Upper limit: utmost 80 or utmost 75 or utmost 70 wt. %;
 Range: from 3 to 80 or from 5 to 75 or from 10 to 70 wt. %.
wt. % with respect to the weight of Paste B.

If the amount of the polyacid is too high, obtaining a workable consistency of the obtained paste when mixing the compositions contained in the kit of parts described in the present text might become difficult. Furthermore, preparation of the compositions might become difficult. In addition, the obtained mixture or composition might become too sticky (i.e. adheres to the dental instrument used for application).

If the amount of the polyacid is too low, obtaining a workable consistency of the obtained paste when mixing the compositions contained in the kit of parts described in the present text might become difficult, either. Furthermore, it might become difficult to achieve the desired mechanical properties.

Paste B contains a non acid-reactive filler B.

According to one embodiment, the non acid-reactive filler B can be characterized by a mean particle size of below about 10 μm.

Examples of suitable non acid-reactive fillers B are naturally occurring or synthetic materials including, but not limited to: silica (e.g., submicron pyrogenic silicas such as those available under the trade designations "AEROSIL™", including "OX 50," "130," "150" and "200", silicas from Degussa AG, Hanau, Germany and HDK, including "H15", "H20", "H2000" from Wacker, Munich, Germany and CAB-O-SIL M5 silica from Cabot Corp., Tuscola, Ill.), quartz, cristobalite (e.g Sikron™ SF 6000), borosilicate glass, alumina, titania and zirconia particles and mixtures thereof.

The particles of the non-acid reactive filler B is typically not surface treated with silanes.

The non acid-reactive filler B is typically present in the following amounts:
 Lower limit: at least 2 or at least 5 or at least 7 wt. %;
 Upper limit: utmost 90 or utmost 80 or utmost 75 wt. %;
 Range: from 2 to 90 or from 5 to 80 or from 7 to 75 wt. %;
wt. % with respect to the weight of Paste B.

If desired, Paste A can also contain a non acid-reactive filler, which may be same or different than the non acid-reactive filler contained in Paste B.

Paste B contains a complexing agent or chelating agent. The terms complexing or chelating agent are used interchangeable.

The nature and structure of the complexing or chelating agent is not particularly limited, either unless the desired result cannot be achieved.

The complexing agent is typically used for adjusting the curing properties of the hardenable composition, in particular for adjusting the working time.

The complexing agent can be characterized by at least one or more or all of the following parameters:
 Solubility: soluble in water (at least 50 g/l water at 23° C.);
 Molecular weight: from 50 to 500 g/mol, or from 75 to 300 g/mol.

Specific examples of the complexing agent include tartaric acid, citric acid, ethylene diamine tetra acetic acid (EDTA), salicylic acid, mellitic acid, dihydroxy tartaric acid, nitrilotriacetic acid (NTA), 2,4 and 2,6 dihydroxybenzoic acid, phosphono carboxylic acids, phosphono succinic acid and mixtures thereof.

Further examples can be found e.g. in U.S. Pat. No. 4,569,954 (Wilson et al.). The content of this document is herewith incorporated by reference.

The complexing agent is typically added to that paste containing the polyacid only, i.e., to Paste B.

The complexing agent is typically present in the following amount:
 Lower limit: at least 0.1 or at least 1.0 or at least 1.5 wt. %;
 Upper limit: utmost 15 or utmost 12 or utmost 10 wt. %;
 Range: from 0.1 to 15 or from 1.0 to 12 or from 1.5 to 10 wt. %;
wt. % with respect to the weight of the Paste B.

Paste B can typically be characterized by either, more or all of the following features:
 Viscosity: from 100 to 50,000 Pa*s (23° C.; 15 mm diameter; shear rate: 20 $s^{-1}$);
 Density: from 1.3 to 2.0 $g/cm^3$;
 pH value: from 1 to 4 (determined with a pH indicator for 1 g paste being dispersed in 10 ml de-ionized water and stirred for about 5 minutes).

Either Paste A or Paste B or Paste A and Paste B of the kit of parts described in the present text can also contain solvent(s).

Adding solvent(s) or co-solvent(s) may help to adjust the viscosity and consistency of the composition.

Examples of solvent(s) which can be used include alcohols (e.g. methanol, ethanol, propanol), polyalcohols/polyols (e.g. polyethylene glycol, ethylene glycol, glycerol) and mixtures thereof.

Either Paste A or Paste B or Paste A and Paste B of the kit of parts described in the present text can also contain additives.

Additives which might be present include indicator(s), dye(s), pigment(s), surfactant(s), buffering agent(s), stabilizer(s), preservative agent(s) (e.g., benzoic acid).

Combination of any of the above additives may also be employed. The selection and amount of any one such additive can be selected by one skilled in the art to accomplish the desired result without undue experimentation.

There is no need for those component(s) to be present, however, if present, the individual component is typically present in an amount of less than 5 wt. % or less than 3 wt. % or less than 1 wt. % with respect to the weight of the respective Paste (A or B).

Useful ranges of those component(s) include from 0.01 to 5 wt. % or from 0.05 to 3 wt. % or from 0.05 to 1 wt. %, wt. % with respect to the weight of the respective Paste A or B.

The invention also relates to a composition obtained when mixing the respective pastes of the kit of parts described in the present text.

According to one embodiment the cement composition obtained or obtainable by mixing the two pastes of the kit of parts described in the present text fulfils at least one or both of the following parameters before or during hardening:
  Setting time: within about 10 or 8 or 6 min;
  Working time: within about 7 or about 5 or 3 min.

If desired, the curing behaviour can be determined as described in more detail in the example section below.

The cement composition described in the present text typically has a sufficient working time allowing the practitioner not only to adequately mix the composition but also to apply the composition to the surface of a crown, bridge, root canal or prepared tooth.

Furthermore, the cement composition described in the present text has an adequate setting time, which is time saving for the practitioner and convenient for the patient.

According to another embodiment the cement composition obtained or obtainable by mixing the two pastes of the kit of parts described in the present text fulfils at least one or more, sometimes all of the following parameters after hardening:
  Flexural strength: above about 20 or above about 25 MPa determined according to EN-ISO 9917-2:2010 with the proviso that for covering the composition a glass slab is used instead of a foil;
  Compressive strength: above about 60 or above about 80 or above about 100 MPa determined according to EN-ISO 9917-1/2007 with the proviso that for covering the composition a glass slab is used instead of a foil.

If desired, these parameters can be determined as described in the example section below.

Compared to state of the art glass ionomer cements available on the market, the cement composition described in the present text can easily be mixed and has adequate mechanical properties like compressive strength without affecting other important parameters like setting time.

The glass ionomer cement composition obtained when mixing Paste A and Paste B of the kit of parts described in the present text can typically be characterized as follows:
comprising water in the following amounts:
  Lower limit: at least 6 or at least 8 or at least 10 wt. %;
  Upper limit: utmost 40 or utmost 35 or utmost 30 wt. %;
  Range: from 6 to 40 or from 8 to 35 or from 10 to 30 wt. %;
comprising the acid-reactive filler A in the following amounts:
  Lower limit: at least 20 or at least 25 or at least 30 wt. %;
  Upper limit: utmost 50 or utmost 45 or utmost 40 wt. %;
  Range: from 20 to 50 or from 25 to 45 or from 30 to 40 wt. %;
comprising the non acid-reactive filler B in the following amounts:
  Lower limit: at least 1 or at least 2 or at least 3 wt. %;
  Upper limit: utmost 50 or utmost 45 or utmost 40 wt. %;
  Range: from 1 to 50 or from 2 to 45 or from 3 to 40 wt. %;
comprising the polyacid in the following amounts:
  Lower limit: at least 1 or at least 2 or at least 5 wt. %;
  Upper limit: utmost 45 or utmost 40 or utmost 35 wt. %;
  Range: from 1 to 45 or from 2 to 40 or from 5 to 35 wt. %;
comprising complexing agent in the following amounts:
  Lower limit: at least 0.05 or at least 0.5 or at least 0.75 wt. %;
  Upper limit: utmost 6 or utmost 5 or utmost 4 wt. %;
  Range: from 0.05 to 6 or from 0.5 to 5 or from 0.75 to 4 wt. %;
comprising phyllo silicate in the following amounts:
  Lower limit: at least 0.05 or at least 0.1 or at least 0.25 or at least 0.5 wt. %;
  Upper limit: utmost 15 or utmost 12 or utmost 10 or utmost 2 wt. %;
  Range: from 0.05 to 15 or from 0.1 to 12 or from 0.25 to 10 or from 0.5 to 2 wt. %.

With respect to the above amounts, the wt. % refers to the weight of the whole composition obtained when mixing the pastes of the kit of parts.

The amount of fillers A and B contained in the composition obtained when mixing Paste A and Paste B is typically above 50 or above 55 or above 60 wt. %.

A high filler content combined with a low water content typically helps to improve mechanical properties of the hardened composition like compressive strength.

The water content of the composition obtained when mixing Paste A and Paste B is below 35 or below 30 wt. %. A low water content typically helps to improve physical properties like compressive strength.

The pastes of the kit of part described in the present text can be produced by simply mixing the individual components of the respective pastes.

If needed, the filler particles can be milled to the desired particle size using equipment known to the skilled person like ball mills.

Mixing can be accomplished either by hand or with a mechanical device like a mixer or kneading machine. The mixing duration can vary depending on the composition and the mixing device and should be sufficiently long to obtain a homogeneous paste.

The kit of parts described in the present text can be provided to the practitioner in different embodiments.

The pastes may be contained in separate sealable vessels (e.g. made out of plastic, glass or metal).

For use, the practitioner may take adequate portions of the pasty components from the vessels and mix the portions by hand on a mixing pad.

According to a preferred embodiment, the pastes are contained in separate compartments of a storing device.

The storing device typically comprises two compartments for storing the respective pastes, each compartment being equipped with a nozzle for delivering the respective paste. Once delivered in adequate portions, the pastes can then be mixed by hand on a mixing pad.

According to another preferred embodiment, the storing device has an interface for receiving a static mixing tip. The mixing tip is used for mixing the respective pastes. Static mixing tips are commercially available e.g. from Sulzer-Mixpac company.

Suitable storing devices include cartridges, syringes and tubes.

The storing device typically comprises two housings or compartments having a front end with a nozzle and a rear end and at least one piston movable in the housing or compartment.

Cartridges which can be used are described e.g. in US 2007/0090079 (Keller) or U.S. Pat. No. 5,918,772 (Keller et al.), the disclosure of which is incorporated by reference. Some of the cartridges which can be used are commercially available e.g. from SulzerMixpac AG (Switzerland). Static mixing tips which can be used are described e.g. in US 2006/0187752 (Keller) or in U.S. Pat. No. 5,944,419 (Streiff), the disclosure of which is incorporated by reference. Mixing tips which can be used are commercially available from SulzerMixpac AG (Switzerland), as well.

Other suitable storing devices are described e.g. in WO 2010/123800 (Boehm et al.), WO 2005/016783 (Reidt et al.), WO 2007/104037 (Broyles et al.), WO 2009/061884 (Boehm et al.), in particular the device shown in FIG. 14. The content of these references is herewith incorporated by reference, as well.

Alternatively, paste/paste compositions described in the present text can be provided in two individual syringes and the individual pastes can be mixed by hand prior to use.

Thus, the invention is also directed to a device for storing the kit of parts described in the present text, the device comprising two compartments, Compartment A and Compartment B, Compartment A containing Paste A and Compartment B containing Paste B, Paste A and Paste B being as described in the present text, Compartment A and Compartment B both comprising a nozzle or an interface for receiving an entrance orifice of a static mixing tip.

The mixing ratio of Paste A and Paste B is typically from 5:1 to 1:5 with respect to volume, preferably from 3:1 to 1:3, even more preferred from 1:1.

Alternatively, the mixing ratio of Paste A and Paste B is typically from 6:1 to 1:6 with respect to weight, preferably from 4:1 to 1:4.

The composition obtained or obtainable when mixing the respective pastes is in particular useful as or for producing a dental cement, dental filling material, dental core build-up material or as dental root channel filling material.

A typical application comprises the following steps:
a) mixing Paste A and Paste B to obtain a hardenable composition,
b) applying the hardenable composition to the surface of hard dental tissue,
c) letting the hardening composition harden.

In addition, the kit of parts described in the present text typically contains an instruction for use.

The instruction for use typically contains hints how to store the kit of parts, mix the pastes of the kit of parts and/or how to apply the composition obtained by mixing the pastes to the surface of hard dental tissue.

According to one embodiment, the invention relates to a kit of parts being characterized as follows:
Paste A comprising
water in an amount from 10 to 35 wt. %,
the acid-reactive inorganic filler A in an amount from 50 to 90 wt. %, the acid-reactive inorganic filler A having a mean particle size in the range from 1 to 15 μm and being selected from metal oxides, metal hydroxides, hydroxyapatite, fluoroaluminosilicate glasses and mixtures thereof,
phyllo silicate selected from 2:1 layer silicates and being present in an amount from 0.5 to 10 wt. %, Paste B comprising
water in an amount from 10 to 45 wt. %,
the polyacid in an amount from 5 to 70 wt. %,
the complexing agent in an amount from 0.1 to 12 wt. %,
the non acid-reactive filler B in an amount from 5 to 70 wt. %, the non acid-reactive filler B having a mean particle size in the range from 0.01 to 15 μm and being selected from quartz, silica, alumina, titanium, zirconia and mixtures thereof,
wt. % with respect to the weight of the respective Paste A or Paste B,
neither Paste A nor Paste B comprising polymerizable component(s) in an amount above 1 wt. % with respect to the weight of the composition obtained when mixing Paste A and Paste B.

Typically, neither Paste A nor Paste B or nor Paste A and Paste B of the kit of parts described in the present text do contain either of the following components alone or in combination:
a) hydroxyl ethyl methacrylate (HEMA) in an amount above 1 wt. % or above 0.5 wt. %;
b) polymerizable component(s) in an amount above 1 wt. % or above 0.5 wt. %;
c) initiator component(s) suitable to cure polymerizable component(s) or monomer(s) in an amount above 1 wt. % or above 0.5 wt. %;
d) inhibitior(s) like methoxyphenol or 3,5-Di-tert-butyl-4-hydroxytoluol in an amount above 1 wt. % or above 0.5 wt. %;
e) desiccant(s) like zeolithe(s) in an amount above 1 wt. % or above 0.5 wt. %
wt. % with respect to the weight of Paste A or Paste B.

Thus, the composition obtained when mixing the powder and liquid part of the kit of parts described in the present text is not a so-called resin-modified glass ionomer cement (RM-GIC) and thus does not contain a curing system based on polymerization.

In particular, the cement composition described in the present text does not contain a redox-initiator system or a thermally induced initiator system or a radiation induced initiator system.

In particular, the cement composition described in the present text does not contain the following components:
(a) and (b),
(b) and (c),
(a), (b) and (c),
(b), (c) and (d),
(a), (b), (c) and (d)
in an amount above 1 wt. % or above 0.5 wt. % or above 0.1 wt. % with respect to the weight of the whole composition.

That is, the cement composition described in the present text is typically essentially free of either of these components alone or in combination.

All components used in the dental composition of the invention should be sufficiently biocompatible, that is, the composition should not produce a toxic, injurious, or immunological response in living tissue.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).

Test Methods

Viscosity of Mixed Pastes

The viscosity of the mixed pastes was measured using a Physica MCR 301 Rheometer (Anton Paar, Graz, Austria) with a plate/plate geometry (PP15) at a constant shear rate in rotation at 23° C. The diameter of the plates was 15 mm and the gap between the plates was set to 0.25 mm. After hand mixing of both pastes in a 1:1 weight ratio for 20 s, the mixture (~160 mg) was placed on the plate. The viscosity was measured 1 min after the start of the hand mixing. One data point was recorded per second. The measuring time was 15 s and the viscosity was determined by averaging the last 5 data points. The viscosity was measured at a shear rate of 200 s$^{-1}$. Every measurement was conducted twice.

Viscosity of Paste B

If desired, the viscosity of Paste B can be measured using a Physica MCR 301 Rheometer (Anton Paar, Graz, Austria) with a plate/plate geometry (PP15) at a constant shear rate of 20 s$^{-1}$ in rotation at 23° C. The diameter of the plates was 15 mm and the gap between the plates is set to 0.25 mm. Paste B (~160 mg) is placed on the plate. One data point is recorded per second. The measuring time is 60 s and the viscosity is determined by averaging the last 5 data points.

Compressive Strength (CS)

Measurement of the compressive strength was carried out according to the EN-ISO 9917-1:2007 with the proviso that for covering the composition a glass slab is used instead of a foil. Cylindrical specimens with a diameter of 4 mm and a height of 6 mm were used. Specimens of the materials were prepared at room temperature and 50% relative humidity using split moulds. The moulds were placed on microscope slides and thoroughly filled with the mixed material to avoid incorporation of air bubbles. The filled moulds were immediately covered with another glass slab and fixed in a screw clamp with slight pressure to extrude excess material. The whole assembly was stored in water at 36° C. 1 h after start of mixing the specimens were removed from the moulds and immediately placed in water at 36° C. 6 specimens were prepared for each material. Materials were measured 24 h after start of mixing. The exact diameter of each specimen was measured prior to the measurement. The strength of the specimen was measured by applying a compressive load using a Zwick universal testing machine (Zwick GmbH & Co. KG, Ulm, Germany) operating at a crosshead speed of 1 mm/min. Results were reported as an average of 6 replications.

Working Time

If desired, working time can be determined according to the following protocol.

Working time of the mixed pastes can be determined using a Physica MCR 301 Rheometer (Anton Paar, Austria) with a plate/plate geometry (PP08) at a constant shear rate in oscillation at 28° C. The diameter of the plates is 8 mm and the gap between the plates is set to 0.75 mm. The paste are hand mixed in a 1:1 weight ratio. About 200 mg of the mixture is then placed on the cylindrical platform. Tan δ is measured in dependency on the time in an oscillating measurement (frequency 1.25 Hz; deformation 1.75%). Afterwards, the working time is calculated using a customized algorithm.

Storage Stability

Storage stability regarding paste separation was determined using a commercially available LUMiFuge 110 device. The device is an analytical centrifuge in which the samples are examined in terms of their space-resolved extinction profile while a strong centrifugal force is applied to them.

The separation stability tests were run for 10 h at an average centrifugal load of app. 2050 g (=4000 rpm). 300 single separation profiles were recorded by measuring a data point after every 120s. Commercially available measurement cells were used (LUM 10 mm, PC, Rect. Synthetic Cell (110-132xx)).

If desired, the sedimentation speed of the samples can be evaluated by measuring the velocity of the movement of the separation line between clear (separated) and opaque phase. The velocity of clarification can be determined between start of the measurement (0 s) and 17,000 s (~5 h running time) using a linear regression. Every measurement is typically conducted twice.

Density

If desired, the density of the pastes can be measured by filling the pastes into a container of defined volume and by weighing the container with and without paste. The weight difference divided by the defined volume yields the density of the paste.

Extrusion Force

If desired, the extrusion force for the glass ionomer cement composition can be measured using as testing device a Zwick Z020 machine (Zwick Roell Comp.). The testing device is equipped with a holder for containers and a small stamp to press against the piston inserted in the container and sealing the reservoir. The dimensions of the stamp corresponded to those used in commercially available single container dispensers. The feeding speed is set to 1.0 mm/s. The force is measured after the initial yield point is overcome (about 6-9 mm from starting point). The extrusion force can be determined as an average value out of six individual measurements.

Particle Size

If desired, the particle size distribution including the mean particle size can be determined with a Cilas 1064 (FA. Quantacrome) particle size detection device. During the measurement, ultrasonic was used to accurately disperse the sample.

Molecular Weight

If desired, the molecular weight (Mw) can be determined by gel permeation chromatography (GPC) against a polyacrylic acid sodium salt standard. In particular the following equipment was found to be useful: PSS SECurity GPC System equipped with 2*PSS Suprema 3000A, 8*300 mm, 10 μm columns; eluent: 84 mM Na2HPO4+200 ppm NaN3; flux rate: 1 ml/min.

Materials

TABLE 1

| Name | Description |
| --- | --- |
| FAS-glass | Acid-reactive filler; powder component of Ketac ™ Molar (from 3M Oral Care; 3M ESPE); mean particle size: 3.84 μm, d10: 0.87 μm, d50: 2.73 μm, d90: 8.80 μm. |

TABLE 1-continued

| Name | Description |
|---|---|
| Cristobalite powder | Non reactive filler; mean particle size: 1.16 μm, d10: 0.41 μm, d50: 0.98 μm, d90: 2.06 μm. |
| Tartaric acid | Complexing agent |
| Polyacid 1 | acrylic acid/maleic acid co-polymer (1:1 co-polymer, Mw = 20,000 g/mol) |
| Polyacid 2 | acrylic acid/maleic acid co-polymer (1:1 co-polymer, Mw = 12,000 g/mol) |
| Sodium Carboxymethyl Cellulose | Paste forming agent; ($M_w$ = 90,000 g/mol) |
| Optigel ™ CK | Paste forming agent; activated bentonite; layer 2:1 phyllo silicate, (BYK-Chemie GmbH) |
| Bentonite | Paste forming agent; mesh <63 μm, 2:1 phyllo silicate |
| Montmorillonite | Paste forming agent; mesh <63 μm, 2:1 phyllo silicate |

Example Preparation

General Preparation of Pastes A (Non Acidic Paste)

The paste forming agents were added to the FAS-glass and the powders were mixed by shaking. Then, the deionized water was added to the powder mixture by hand mixing. The mixture was mixed by using a commercially available SpeedMixer™ DAC 150 SP (Hauschild, Germany) by application of 1× 90 s, 2700 RPM. The paste is stored in an alumina tube to prevent loss of water due to drying out.

General Preparation of Paste B (Acidic Paste)

Preparation of Polyacrylic Acid Solution 15.2 g of the Polyacid 1 was added to 24.8 g of an aqueous solution of 44 wt. % of Polyacid 2, 9.1 wt. % tartaric acid and 0.1 wt. % benzoic acid by hand mixing. Then, the mixture was mixed by using a commercially available SpeedMixer™ DAC 150 SP (Hauschild, Germany) by application of 90 s, 3000 RPM. Polyacid 1 was allowed to completely dissolve overnight. Afterwards, the mixture was again mixed (90 s, 3000 RPM).

Preparation of Paste B 30.0 g of non acid-reactive filler (Cristobalite powder) was added to 35.0 g of the above described polyacrylic acid solution by hand mixing. Then, the mixture was mixed by using a commercially available SpeedMixer™ DAC 150 SP (Hauschild, Germany) by application of 2× 90 s, 2700 RPM and 1× 15 s 2300 RPM (cooling to room temperature after each mixing step). The paste was stored in an alumina tube to prevent loss of water due to drying out.

Glass Ionomer Compositions

Compositions

The following examples demonstrate the effect of the described paste forming agents in different amounts. In this respect, a part of the FAS-glass has been replaced by the paste forming agent in the stated amount.

TABLE 2

| Non acidic paste | Na-Carboxy methyl cellulose (wt. %) | Montmorillonite (wt. %) | Bentonite (wt. %) | Optigel CK (wt. %) | FAS Glass (wt. %) | Deionized Water (wt. %) |
|---|---|---|---|---|---|---|
| A1 | — | — | — | — | 1.5 | 75.7 | 22.8 |
| A2 (comp.) | 1.5 | — | — | — | 75.7 | 22.8 |
| A3 (comp.) | — | — | 3.9 | — | 73.3 | 22.8 |
| A4 | — | — | — | 3.9 | 73.3 | 22.8 |
| A5 (comp.) | 3.9 | — | — | — | 73.3 | 22.8 |
| A6 (comp.) | — | 9.2 | — | — | 67.8 | 23.0 |

TABLE 2-continued

| Non acidic paste | Na-Carboxy methyl cellulose (wt. %) | Montmorillonite (wt. %) | Bentonite (wt. %) | Optigel CK (wt. %) | FAS Glass (wt. %) | Deionized Water (wt. %) |
|---|---|---|---|---|---|---|
| A7 | — | — | — | 9.2 | 67.8 | 23.0 |
| A8 (comp.) | 9.2 | — | — | — | 67.8 | 23.0 |

Composition of Paste B1 (Acidic Paste)

TABLE 3

| Cristobalite powder | 46.2 |
| Polyacid 1 | 20.4 |
| Polyacid 2 | 14.5 |
| Water | 15.87 |
| Tartaric acid | 3.0 |
| Benzoic acid | 0.03 |

Example Mixtures

TABLE 4

| Example | Non acidic paste | Acidic Paste | Mixing Ratio (weight) |
|---|---|---|---|
| 1 | A1 | B1 | 1:1 |
| 2 (comp.) | A2 | B1 | 1:1 |
| 3 (comp.) | A3 | B1 | 1:1 |
| 4 | A4 | B1 | 1:1 |
| 5 (comp.) | A5 | B1 | 1:1 |
| 6 (comp.) | A6 | B1 | 1:1 |
| 7 | A7 | B1 | 1:1 |
| 8 (comp.) | A8 | B1 | 1:1 |

The respective compositions were obtained by mixing the respective pastes in a 1:1 (by weight) mixing ratio by hand using a spatula and a mixing pad.

The obtained compositions were analysed with respect to their physical/mechanical properties.

TABLE 5

| Example | Viscosity at 200 s$^{-1}$ [Pa*s] | Compressive strength [MPa] | Standard deviation [MPa] |
|---|---|---|---|
| 1 | 26 | 146 | 10 |
| 2 (comp.) | 58 | 152 | 9 |
| 3 (comp.) | 29 | 153 | 10 |
| 4 | 26 | 150 | 8 |
| 5 (comp.) | 124 | 154 | 5 |
| 6 (comp.) | 35 | 123 | 2 |
| 7 | 43 | 149 | 7 |
| 8 (comp.) | 242 | 138 | 9 |

Separation Stability (Non Acidic Pastes)

TABLE 6

| Non acidic paste | Separation velocity at 4000 rpm [μm/s] | Standard deviation [μm/s] |
|---|---|---|
| A1 | 0.015 | 0.005 |
| A2 | 0.093 | 0.008 |

The force needed to handmix the pastes according to the invention was lower than the force needed for mixing the pastes of the comparative example, as can be retrieved from the viscosity values (for high shear rates).

Furthermore, both pastes could be mixed in a convenient 1:1 ratio, allowing for predictable clinical outcomes.

The glass ionomer cements according to the invention also showed adequate mechanical properties, as demonstrated by the compressive strength values.

As can be taken from the value of the separation velocity, the non acidic Paste A according to the invention also showed better storage stability compared to the non acidic Paste A of the comparative example (as can be retrieved from the separation analysis).

What is claimed is:

1. A kit of parts for preparing a glass ionomer composition for dental use, the kit comprising a Paste A and a Paste B,
    Paste A comprising:
        water,
        acid-reactive inorganic filler A,
        phyllo silicate(s), the phyllo silicate being selected from 2:1 layer silicates comprising calcium ions and sodium ions,
    Paste B comprising:
        water,
        polyacid,
        non acid-reactive filler B,
        optionally chelating agent.

2. The kit of parts of claim 1, the phyllo silicates being selected from talc-pyrophyllite minerals, smectite minerals, vermiculite minerals, illites minerals, glimmer minerals, mica minerals and mixtures thereof.

3. The kit of parts of claim 1, the phyllo silicates being selected from montmorillonite, bentonite, hectorite, talc, willemseite, pyrophyllite, stevensite, saponite, sauconite, beidellite, nontronite, volkonskite, phlogopite, biotite, lepidolite, muscovite, illite, glauconite, celadonite, and mixtures thereof.

4. The kit of parts of claim 1, the phyllo silicate being used in an amount of 0.1 to 30 wt. % with respect to the weight of Paste A.

5. The kit of parts of claim 4, Paste A being characterized by at least one or more of the following parameters:
    density: from 1.5 to 3.0 g/cm$^3$;
    pH value: from 5 to 10 determined with a pH indicator for 1 g Paste A dispersed in 10 ml de-ionized water and stirred for 5 min.

6. The kit of parts of claim 1, Paste B being characterized by at least one or more of the following parameters:
    viscosity: from 100 to 50,000 Pa*s at 23° C., measured at a shear rate of 20 s$^{-1}$;
    density: from 1.3 to 2.0 g/cm$^3$;
    pH value: from 1 to 4 determined with a pH electrode for 1 g of Paste B dispersed in 10 ml de-ionized water and stirred for 5 min.

7. The kit of parts of claim 1, the water content of the composition obtained when combining Paste A and Paste B being below 30 wt. %.

8. The kit of parts of claim 1, neither Paste A nor Paste B comprising
    at least one or more or all of the following components:
        polymerizable component(s) in an amount above about 1 wt. %;
        initiator component(s) suitable to cure polymerizable component(s) in an amount above 1 wt. %;
        2-hydroxyethyl cellulose, sodium alginate, or sodium carboxymethyl cellulose in an amount above about 0.5 wt. %;
    wt. % with respect to the weight of the respective Paste A or Paste B.

9. The kit of parts of claim 1, being characterized as follows:
    Paste A comprising:
        water in an amount from 10 to 35 wt. %,
        the acid-reactive inorganic filler A in an amount from 50 to 90 wt. %, the acid-reactive inorganic filler A having a mean particle size in the range from 1 to 15 µm and being selected from metal oxides, metal hydroxides, hydroxyapatite, fluoroaluminosilicate glasses and mixtures thereof,
        phyllo silicate being a 2:1 layer silicate and being present in an amount from 0.5 to 10 wt. %,
    Paste B comprising:
        water in an amount from 10 to 45 wt. %,
        the polyacid in an amount from 5 to 70 wt. %,
        the chelating agent in an amount from 0.1 to 12 wt. %,
        the non acid-reactive filler B in an amount from 5 to 70 wt. %, the non acid-reactive filler B having a mean particle size in the range from 0.01 to 15 µm and being selected from quartz, silica, alumina, titania, zirconia and mixtures thereof,
    wt. % with respect to the weight of the respective Paste A or Paste B,
    neither Paste A nor Paste B comprising polymerizable component(s) in an amount above 1 wt. % with respect to the weight of the composition obtained when mixing Paste A and Paste B.

10. A hardened composition for dental use, the hardened composition being obtainable or as obtained by mixing Paste A and Paste B of the kit of parts described in claim 1, letting the mixture harden, the hardened composition being characterized by at least one or more of the following parameters:
    Flexural strength: above 20 MPa determined according to EN-ISO 9917-2:2010;
    Compressive strength: above 60 MPa determined according to EN-ISO 9917-1/2007.

11. A device for storing the kit of parts of claim 1, the device comprising two compartments, Compartment A and Compartment B, Compartment A containing Paste A and Compartment B containing Paste B, Paste A and Paste B as described in claim 1, Compartment A and Compartment B both comprising a nozzle or an interface for receiving an entrance orifice of a static mixing tip.

12. A method for preparing a glass ionomer cement, the method comprising:
    providing a kit of parts of claim 1,
    contacting Paste A with Paste B to provide the glass ionomer cement.

13. A method of preparing a glass ionomer cement paste composition, the method comprising:
    providing a phyllo silicate selected from 2:1 layer silicates comprising calcium ions and sodium ions, water, and an acid-reactive inorganic filler,
    mixing the phyllo silicate, water, and acid-reactive inorganic filler to provide the glass ionomer cement paste composition.

14. The method of claim 12, wherein the glass ionomer cement is a dental cement, a dental filling material, a dental core build-up material, or a dental root channel filling material.

15. The method of claim 12, further comprising hardening the glass ionomer cement.

* * * * *